(12) United States Patent
Brodkin et al.

(10) Patent No.: US 7,691,497 B1
(45) Date of Patent: Apr. 6, 2010

(54) PRESSABLE OVERLAY MATERIAL FOR VENEERING OF ZIRCONIA AND COMPOSITES THEREOF

(75) Inventors: Dmitri G. Brodkin, Livingston, NJ (US); Anna B. Verano, Jersey City, NJ (US)

(73) Assignee: Ivoclar Vivadent, Inc. (LI)

( * ) Notice: Subject to any disclaimer, the term of this patent is extended or adjusted under 35 U.S.C. 154(b) by 433 days.

(21) Appl. No.: 11/785,042

(22) Filed: Apr. 13, 2007

(51) Int. Cl.
*B32B 17/06* (2006.01)

(52) U.S. Cl. ........................................ 428/701

(58) Field of Classification Search ........... 428/701
See application file for complete search history.

(56) References Cited

U.S. PATENT DOCUMENTS

| | | | |
|---|---|---|---|
| 4,793,809 | A | 12/1988 | Sigler et al. |
| 5,614,330 | A | 3/1997 | Panzera et al. |
| 5,788,498 | A | 8/1998 | Wohlwend |
| 5,833,464 | A | 11/1998 | Foser |
| 5,849,068 | A | 12/1998 | Hofmann et al. |
| 5,916,498 | A | 6/1999 | Hofmann et al. |
| 6,126,732 | A | 10/2000 | Hofmann et al. |
| 6,302,186 | B1 | 10/2001 | Vidal |
| 6,306,784 | B1 | 10/2001 | Drescher et al. |
| 6,484,791 | B1 | 11/2002 | Vidal |
| 6,554,615 | B1 | 4/2003 | Brodkin et al. |
| 6,626,986 | B2 | 9/2003 | Schweiger et al. |
| 6,709,694 | B1 | 3/2004 | Suttor et al. |
| 6,984,261 | B2 * | 1/2006 | Cummings et al. ....... 433/222.1 |
| 2004/0232576 | A1 | 11/2004 | Brodkin et al. |
| 2006/0099552 | A1 | 5/2006 | van der Zel et al. |

FOREIGN PATENT DOCUMENTS

EP 0231773 8/1987

OTHER PUBLICATIONS

F. Filser et al., "All-Ceramic Dental Bridges by Direct Ceramic Machining (DCM)", *Materials in Medicine, Materials Day, Department of Materials*, Eds. MO. Speidel, P.J. Uggowitzer, vdf Hochschulverlag AG, ETH, Zürich, May 1998, pp. 165-189.

* cited by examiner

*Primary Examiner*—Gwendolyn Blackwell
(74) *Attorney, Agent, or Firm*—George R. McGuire; Ann M. Knab; Bond Schoeneck & King, PLLC

(57) ABSTRACT

A pressable body is described possessing a flexural strength of at least 125 MPa and is flowable at about 850° C. to about 950° C. The body is composed of at least a glass matrix phase having a composition comprising $Li_2O$ and MgO. A dental article formed at least in part from the pressable body is also described. Associated methods are also described.

41 Claims, 4 Drawing Sheets

PRESSABLE OVERLAY MATERIAL FOR VENEERING OF ZIRCONIA AND COMPOSITES THEREOF

FIELD OF THE INVENTION

The present invention is directed to materials possessing certain compositions and properties that render them suitable for a number of applications. For example, materials of the present invention can be utilized as overlay materials for dental articles. According to certain aspects, the present invention is also directed to techniques and methods associated with the above materials.

BACKGROUND

In the discussion that follows, reference is made to certain structures and/or methods. However, the following references should not be construed as an admission that these structures and/or methods constitute prior art. Applicant expressly reserves the right to demonstrate that such structures and/or methods do not qualify as prior art.

Overlay materials are used in dentistry in order to obtain natural-looking dental restorations. Glass-ceramics, also known as porcelains in the art, and certain glasses, are desirable for this purpose since they can be colored to closely resemble the teeth they must replace, resist degradation inside the oral cavity, and remain biocompatible even after years of continuous contact with mammalian tissue. The term "dental ceramics," is usually used to refer to both glass and glass-ceramic overlay materials, as well as glass-ceramic and crystalline ceramic materials used for dental restoration cores and frameworks. The term "porcelain" is often used interchangeably with the term "glass ceramic" to designate dental ceramics comprising both glass and crystalline phases. Dental restorations or prostheses comprising dental ceramics may be classified as either metal-ceramic or as all-ceramic restorations.

Today, there is an increasing trend in dentistry toward the use of ceramic cores or frameworks in lieu of metal alloy frameworks to provide an all-ceramic dental restoration, which is associated with better aesthetics and biocompatibility.

Yttria stabilized tetragonal zirconia polycrystalline (YTZP) has emerged as a high-strength core or framework material for aesthetic dental restorations (e.g., crowns, partial crowns and bridges). In particular, shaded YTZP frameworks have become favored for their aesthetic appeal in the fabrication of all ceramic dental restorations. Consequently, a large number of CAD/CAM systems capable of fabricating YTZP zirconia frameworks have entered the market. Because of high costs of acquiring and operating CAD/CAM systems an alternative trend has emerged. Namely, analog mechanical systems capable of fabricating oversized shapes from partially sintered zirconia using pantograph-like devices, which is described, for example, in U.S. Pat. No. 5,788,498. The accuracy of these relatively low-tech devices is inferior to the state of the art CAD/CAM systems.

However, even the best CAD/CAM system is not able to match pressable ceramics in terms of accuracy of margin adaptation. Quality and accuracy of margins, i.e., margin fit, delivered by alternative pantograph-based systems are not even remotely comparable to benchmarks achievable by heat pressing methods.

Another issue that complicates the fabrication of an aesthetically superior restoration with a zirconia core is the fact that most of the systems require a liner as an intermediate layer between zirconia cores or frameworks and an overlay ceramic. The liner imparts or modifies the color of the framework which is often stark white, and also improves the bonding between the overlay and zirconia. However this liner, which thickness often approaches 0.1 mm, reduces the perceived translucency of the zirconia core and takes invaluable clinical space required for layering.

U.S. Patent Application Publication 2004/0232576 teaches making pressable pellets or ingots from dental porcelain powders comprising alumo-boro-silicate glass and pressing these pellets onto various cores/frameworks including zirconia cores using conventional heat pressing techniques and a commercial dental pressing furnace. These pressable materials have a coefficient of thermal expansion (CTE) in the range of $7\text{-}13 \times 10^{-6}/°$ C. The maturing temperatures and therefore pressing temperatures of dental porcelain compositions disclosed in this publication are less than about 850° and are not optimal for pressing onto YTZP frameworks. It is also difficult to mass produce pellets or ingots from powders comprising low-fusing glasses (with maturing temperature <850° C. as taught in US 2004/0232576) due to difficulties in clean binder removal without graying.

U.S. Patent Application Publication 2006/0099552 teaches heat pressing of tooth colored glass onto YTZP frameworks wherein pressing temperatures are in the range of 750°-1000° C. Glasses disclosed in both patent applications are known to be inherently weak and thus limit the strength of the resulting overlay.

On the other hand, margin porcelains are known to have a relatively high flexural strength, in the range of 120-150 MPa, compared to conventional overlay porcelains. It is also a well known concern among clinicians that an overlay is a weak link in a zirconia-core dental restoration which can limit the structural integrity and life span of the restoration. Therefore, if a pressable overlay material is also used for pressing margins it is extremely desirable that it has strength comparable to or exceeding that of margin porcelains.

It should be noted that "heat pressing," also known as (low pressure) injection molding in the art and commonly referred to as simply "pressing," is different from "hot pressing." Conventional heat pressing is widely used in commercial dental labs in conjunction with mass-produced equipment and requires relatively low pressures of 0.2-0.7 MPa. Hot pressing, despite having a nearly identical name, requires more sophisticated and often experimental or unique equipment and 20-100 times higher pressures, i.e., in the range of 10-100 MPa. Heat pressing is well described in U.S. Pat. Nos. 6,484,791 and 6,302,186. Hot pressing as it relates to fabrication of dental restorations is described in U.S. Pat. Nos. 5,849,068, 5,916,498 and 6,126,732. These patents teach hot pressing of mixtures of oxide ceramics particles and from 1 wt. % to 50 wt. % of glass particles which were added to impart some pressability, at least at high pressures. Pressing takes place at temperatures from 800° C.-1300° C. and pressures from 10 MPa to 40 MPa. The materials disclosed in the above patents are not pressable using conventional pressing technique because they comprise 50-99 wt % of crystalline oxide ceramics particles which inhibit flow under low pressures, but are used to provide a relatively high strength exceeding 300 MPa.

The aforementioned U.S. Pat. Nos. 5,788,498 and 5,833,464 teach hot-pressing a dental ceramic onto prefabricated ceramic reinforcement members, or a pin/post, respectively. Both patents claim zirconia (zirconium oxide) as the preferred material for reinforcement member or pin/post. It should be noted that the reinforcing members and pin/post construction described in these patents are distinct from the core and framework construction of the present invention.

Thus, a need exists in the art for pressable overlay materials for various uses, such as for pre-shaded YTZP zirconia frameworks that do not require use of a liner and have sufficient strength to fabricate 360° overlays, or at least buccal/labial porcelain margins yielding the required variety of shades consistently and without compromise in the structural integrity of the resulting dental restoration. A need also exists for the ability to press an overlay material directly onto YTZP cores or frameworks resulting in net shape, full contour dental restorations with fully formed margins, occlusal and mesiodistal surfaces wherein shade, translucency, CTE and strength of the pressed overlay are optimized, thereby eliminating a porcelain layering step to form such margins and/or surfaces from separate materials. Moreover, a need exists to carry out pressing in the temperature range that is most favorable for YTZP cores or frameworks, thereby promoting retention of their high strength.

SUMMARY

The present invention provides techniques and arrangements that can optionally address one or more of the abovementioned shortcomings associated with conventional technology.

According to one optional aspect of the present invention there is provided a body comprising: a flexural strength of at least 125 MPa; is flowable at about 850° C. to about 950° C.; and at least a glass matrix phase having a composition comprising $Li_2O$ and MgO.

According to another aspect, the present invention provides a dental article comprising: a first member formed from a ceramic; and an overlay attached to the first member, the overlay formed from a material comprising: a flexural strength of at least 125 MPa; is flowable at about 850° C. to about 950° C.; and comprising at least a glass matrix phase having a composition comprising $Li_2O$ and MgO.

According to yet another aspect, there is provided a method of forming a dental article, the method comprising: (a) forming a first member from a ceramic; (b) forming a pressable body from an overlay material comprising a flexural strength of at least 125 MPa; and at least a glass matrix phase having a composition comprising $Li_2O$ and MgO; and (c) heating the body to a temperature of about 850° C. to about 950° C. and pressing the body, thereby causing the overlay to flow onto the first member.

The pressable body described above may optionally be supplied as blanks, pellets or ingots that are pressable at pressures of less than 1 MPa, preferably less than 0.7 MPa, using conventional heat pressing or low-pressure injection molding techniques.

BRIEF DESCRIPTION OF THE DRAWING FIGURES

DETAILED DESCRIPTION

Figure 1:
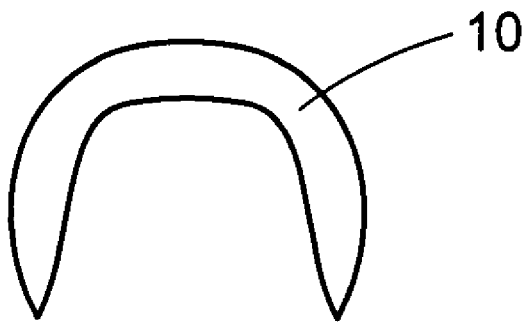
FIG. 1 is a plan view of a ceramic core or framework.

The overlay materials of the present invention possess certain properties and characteristics which render them well-suited for use in the construction of dental articles including all types of dental restorations and dental prostheses and parts thereof such as implant abutments. However, it should be understood that the present invention is not so limited. For example, the materials of the present invention would be expected to be well-suited for other uses such as structural elements of other medical devices such as prosthetic devices for bone and joint replacements.

Overlay material compositions of the present invention may comprise $Li_2O$ as it had been found that even small percentage of $Li_2O$ in the material assures good wetting of a wide variety of ceramic substrates, especially zirconia.

Binders are typically required for the mass-production of blanks, pellets, ingots and the like. It has been observed that low-temperature fusing glasses containing $Li_2O$ can be resistant to complete binder removal resulting in graying of the pellets/ingots upon sintering. It was empirically found that certain elements like $Al_2O_3$, MgO and ZnO will reduce this sensitivity to graying, while $B_2O_3$ in excess of 3 wt. % renders $Li_2O$-containing glasses useless for mass-production of certain articles due to graying upon binder addition. It was also found that $B_2O_3$ is detrimental in combination with $TiO_2$ and $ZrO_2$. Therefore, compositions including combinations of $Li_2O$, $B_2O_3$ with $TiO_2$ and $ZrO_2$ are less favored in the materials of the invention. Compositions including combinations of $Li_2O$ and MgO are favored. Compositions including combinations of $Li_2O$, MgO, and one or more of $Y_2O_3$ and $Al_2O_3$ are also favored according to the principles of the present invention.

According to one exemplary embodiment, an overlay material can have a composition comprising about 0.5-about 2.0 wt. % $Li_2O$, about 0.5-about 3.0 wt. % MgO, and about 0.15-about 1.0 wt. % $Y_2O_3$. According to a further optional embodiment, the above composition may further include about 5-about 20 wt. % $Al_2O_3$. The balance of composition is primarily $SiO_2$ in the amount of 55-80 wt %.

According to another optional embodiment, the overlay material may have a composition that further comprises one or more of the following additional constituents in about the following approximate amounts: 0-7 wt. % $K_2O$, 0-15 wt. % $Na_2O$, 0-3% CaO, 0-3% BaO, 0-3% SrO, 0-3% $CeO_2$, 0-3% $Tb_4O_7$.

According to a further embodiment, the overlay material may comprise an addition of about 0.01-about 1.00 wt. % coloring agent(s). Suitable coloring agents include conventional inorganic pigments such as single or multi-component and multiphase oxides, silicates, spinels, vanadates, manganates, chromates, or other transition metal compounds.

According to still another embodiment of the present invention, an overlay material can be formed which comprises a glass matrix with a composition formulated according to the above-stated principles, in combination with one or more reinforcing filler materials. By way of illustrative nonlimiting examples, the filler may comprise one or more of leucite glass-ceramics, alumina, or leucite-free glass-ceramic materials. The filler may be present in any suitable amounts. For example, the material may comprise from about 1 to about 10 wt. % filler. The filler can be chosen such that it possesses a CTE which differs from the CTE of the glass matrix by at least $1.5 \times 10^{-6}/°$ C. (from about room temperature to about 500° C.). According to another aspect of the present invention, the particle size of the reinforcing filler can be selected such that it is at least six times smaller than the particle size of the particles used to form the glass matrix.

According to another aspect, the present invention is directed to a body which is formed from a material of the type described above. As an illustrative example, overlay materials can be formed into pellets, ingots, cylinders and the like (see, e.g., FIG. 4). These bodies are then heated and pressed to render them flowable. The flow of the overlay material is then directed onto one or more surfaces of a substrate material.

These bodies can be formed by any suitable technique. Such techniques are generally known to those skilled in the art. As a nonlimiting illustration, the constituent components or precursors of the material may be blended, preferably in a finely divided powder form, and heated to a suitable temperature. The thus formed molten material can then be quenched in water, dried, and ground using a suitable milling technique. This reduces the material to a powder form. The powder can then be screened, or subjected to any suitable classification technique, in order to render the particle size within the required range. Various other constituent components can be added to the powder, such additional materials may include one or more of opacifiers, pigments, fluorescing agents, binder materials, fillers and the like. This powdered mixture can then be pressed into a suitable shape, as is per se well-known in the art. The pressed body is then fired at a suitable temperature in order to promote densification.

According to an additional aspect, the present invention is directed to a dental article which is formed, at least in part, from a material of the type described above. For example, the present invention encompasses dental prosthesis or restorations (see, e.g., FIG. 6) formed at least in part from the material described herein. Dental articles encompassed by the present invention include, but are not limited to: crowns, partial crowns, bridges, fixed partial dentures, Maryland bridges, and abutments. By way of nonlimiting example, a dental article formed according to the principles of the present invention may comprise a ceramic core or framework having the overlay material bonded to at least one surface thereof. The ceramic core or framework can be formed of any suitable ceramic material. One such suitable ceramic material comprises YZTP. Other suitable materials include other types of crystalline oxide ceramics and composites thereof such as alumina and alumina-zirconia composites known as alumina-toughened zirconia or ATZ and zirconia-toughened alumina or ZTA.

According to one embodiment, the overlay material is directly bonded to at least one surface of the core, i.e., there is no intervening liner between the core and the overlay material. According to certain embodiments, dental articles formed according to the present invention comprises 360° margins or buccal/labial margins which are formed by the overlay material. According to other embodiments, in addition to the 360° or buccal/labial margins, the dental articles further comprise occlusal and mesio-distal surfaces also formed by the overlay material. Thus, a dental article of the present invention advantageously avoids the necessity of applying a separate material to form the margins of the dental article. This can greatly simplify the process of constructing such articles. Thus, according to the present invention, a net shape dental article can be provided by a single pressing operation utilizing a single overlay material. Exemplary embodiments are illustrated in FIGS. 7-12.

Figure 7:
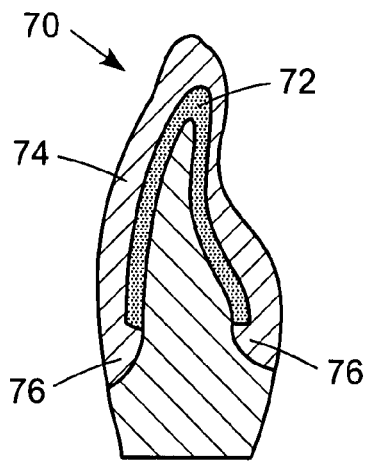
FIG. 7 is a sectional view of a 360° margin on an anterior tooth.

As illustrated in FIG. 7, and anterior tooth 70 formed according to one embodiment of the present invention includes a core or framework 72 within the overlay 74 directly bonded thereto which comprises a 360° margin 76.

Figure 8:
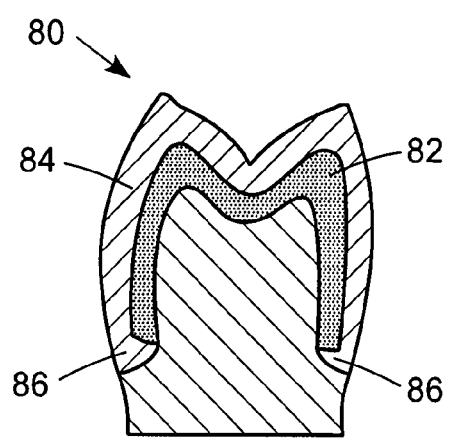
FIG. 8 is a sectional view of a 360° margin on a posterior tooth.

A posterior tooth 80 formed according to an alternative embodiment of the present invention is illustrated in FIG. 8. According to this embodiment, the core or framework 82 comprises an overlay 84 bonded directly thereto having a 360° margin 86.

Figure 9:
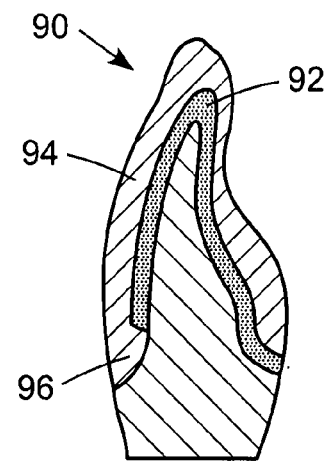
FIG. 9 is a sectional view of a labial margin.

As illustrated in FIG. 9, an anterior tooth 90 formed according to an alternative embodiment of the present invention can be provided with a core or framework 92 having an overlay 94 directly bonded thereto with a labial margin 96.

Figure 10:
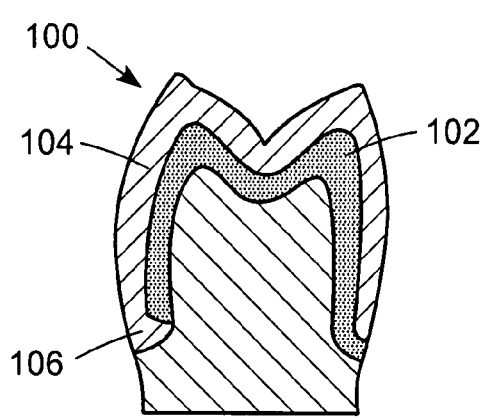
FIG. 10 is a sectional view of a buccal margin.

A posterior tooth 100 formed according to another embodiment of the present invention is illustrated in FIG. 10. As illustrated therein, the tooth 100 comprises a core or framework 102 having an overlay 104 bonded directly thereto and having a buccal margin 106.

Figure 11:
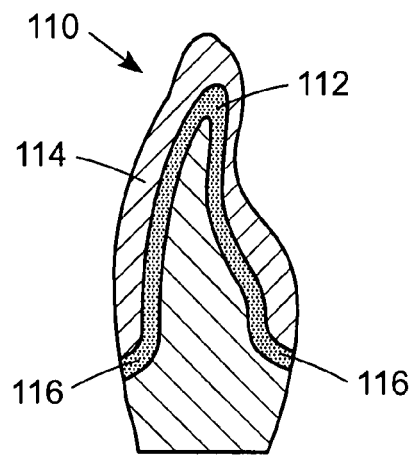
FIG. 11 is a sectional view of a 360° zirconia collar on an anterior tooth.

As illustrated in FIG. 11, an anterior tooth 110 formed according to a further embodiment of the present invention includes a core or framework 112 provided with a 360° collar 116. The overlay 114 is bonded to the core framework 112.

Figure 12:
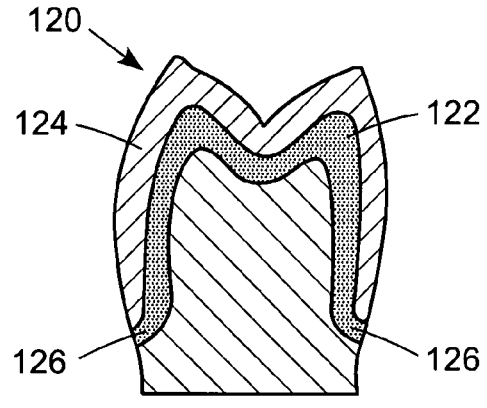
FIG. 12 is a sectional view of a 360° zirconia collar on a posterior tooth.

A posterior tooth 120 formed according to yet another embodiment of the present invention is illustrated in FIG. 12. As illustrated therein, the tooth 120 comprises a core or framework 122 which is provided with a 360° collar 126. The overlay 124 is directly bonded to the core framework 122.

Overlay materials of the present invention may also be provided with one or more properties or characteristics. For example, and overlay material of the present invention can be provided with a flexural strength of at least 125 MPa. The flexural strength property of the present invention is measured by a 3-point or 4-point bend test performed according to the ISO 6872 standard for dental ceramics. Alternatively, in some examples, a 3-point bend test was performed on a rod constructed by pressing a pellet formed by the overlay material of the present invention. It is noted that each of these methods typically yield very similar values for flexural strength of overlay materials of the present invention.

The overlay material of the present invention can be provided with a suitable coefficient of thermal expansion (CTE) which is designed to be compatible with the CTE of the core or reinforcement. By way of nonlimiting example, the overlay material can be provided with a CTE of about $9\text{-}10 \times 10^{-6}/°$ C. (from about room temperature to about 500° C.).

Overlay materials of the present invention may be constructed such that they can be made flowable at temperatures on the order of about 850° C. to about 950° C., under the application of typical pressing pressures which can be on the order of less than about 1.0 MPa, or about 0.2-about 0.7 MPa, or about 0.3-about 0.6 MPa.

There are a few important factors specific to YTZP zirconia that can be considered when defining the optimal pressing temperature for overlay materials. The strength of YTZP drops rapidly at temperatures above 500° C. Above 1000° C. YTZP retains only about 20% of its ambient temperature strength. Grinding or even sandblasting of fully-sintered YTZP cores or frameworks causes transformation of some of tetragonal zirconia grains on or close to the surface to the monoclinic form which is believed to be associated with deterioration of overall mechanical properties. This "skin" affected by transformation can contain as much as 3%-20% of the monoclinic zirconia. Annealing at temperatures above about 600° C. will convert at least part of the transformed zirconia back to tetragonal form. The higher the temperature above the transformation temperature of ~570° C., the faster is the diffusion process of transforming monoclinic zirconia back to its tetragonal form. It is believed that such annealing treatment prior to or in conjunction with applying porcelain to be beneficial for overall mechanical properties of zirconia restoration.

In production lab environments sandblasting and often grinding of zirconia frameworks prior to pressing is practically unavoidable despite manufacturer's recommendations and warnings against it. It is important to note that while most would agree that post-sintering mechanical abuse of zirconia cores or frameworks should be minimized, there is little or no agreement as to whether sandblasting with alumina particles at pressures below 60 psi affects YTZP frameworks negatively or positively.

Improved bonding to zirconia is extremely desirable. Thus, despite the potentially adverse effect on mechanical properties of YTZP cores or frameworks, roughening of the surface thereof by sandblasting may in fact improve bonding/adhesion to zirconia. Adhesion to zirconia cores may be also enhanced by presence of certain components in the overlay material.

The surface of fully-sintered zirconia frameworks may undergo significant microstructural changes during processing in a dental lab. Mechanical abuse (like trimming, grinding, polishing and sandblasting) induces surface transformation of tetragonal zirconia to its monoclinic form. Grinding also "scars" the surface, introducing strength limiting surface flaws, while sandblasting at relatively low pressures of 30-60 psi creates compressive layer than can actually be beneficial. Inadvertent annealing during pressing or firing of porcelain may alleviate some of these detrimental effects of mechanical abuse. Accordingly, the present invention takes advantage of annealing of zirconia during heated pressing to induce a beneficial tempering effect concurrent with pressing operations.

It is important to note that overlay materials of the invention bond equally well to both as-fired and sandblasted zirconia cores or frameworks. It is also important to note that the preferred pressing temperatures of pressable overlays of this invention, i.e., 850°-950° C., facilitate the beneficial "tempering" of zirconia during the pressing procedure.

The embodiments depicted in FIGS. 1-6 are illustrative of certain aspects of the present invention that are described above. Generally, FIGS. 1-6 illustrate a pressable body formed according to the present invention, a dental article formed according to the present invention, a method which utilizes a pressable body formed according to the present invention, and a method of making a dental article according to the present invention. As previously noted, these aspects of the present invention are optional. Overlay materials of the present invention can take forms different from those illustrated in the drawing figures, and can be utilized in methods which also differ from that of the drawing figures.

FIG. 1 is illustrative of a ceramic core or framework 10 which can be utilized in conjunction with the present invention. The core or framework 10 can be formed from any suitable material. According to one embodiment, the core or framework 10 is formed from YTZP. The geometry of the core or framework 10 shown in FIG. 1 is for purposes of illustration only. Thus, the present invention should not be construed as being limited to a particular geometry or configuration.

Cores or frameworks can be formed according to any suitable shaping technique. For example, the outer shape of a resin model of a core or framework is mechanically digitized with a 3-D sensor resulting in a digital representation of surface data points. These surface data points are enlarged in order to compensate for shrinkage which occurs during sintering. Cutting tool path information is generated from the set of data points and transferred to a milling machine. The core or framework is milled from a homogeneous porous ceramic point of ceramic material. After machining, the body is finally sintered to full density.

Figure 2:
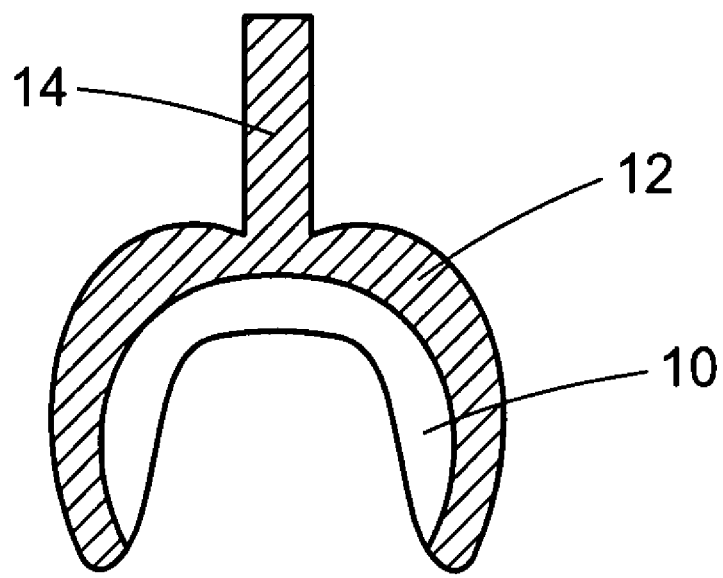
FIG. 2 is a plan view of the core or framework of FIG. 1, with a wax build-up applied thereto.

The core or framework 10 can be used as the foundation of a dental article. According to conventional techniques, wax 12 can be applied to the core or framework 10 which substantially corresponds to the final shape of the dental article or prosthesis, as illustrated in FIG. 2. A sprue 14 can also be formed concurrently from the wax or formed from a separate member and attached thereto.

Figure 3:
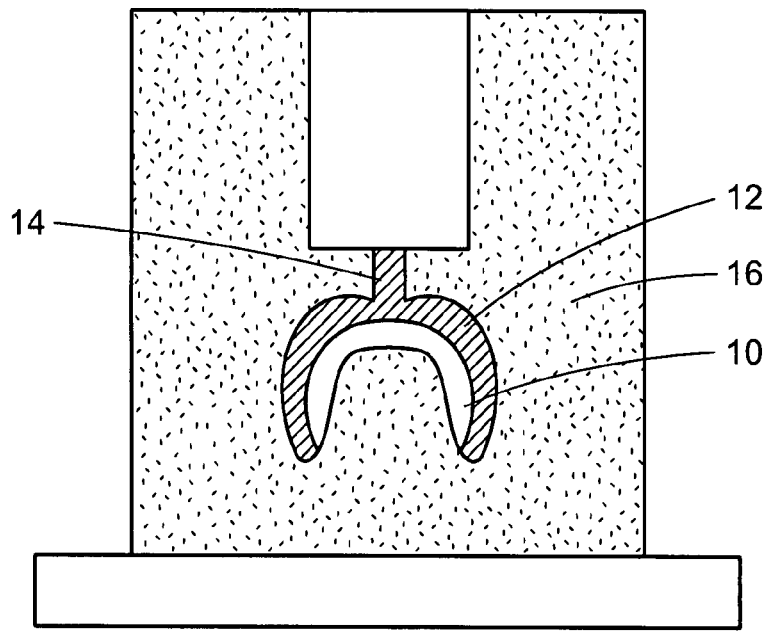
FIG. 3 is a plan view of an arrangement including the built-up core or framework of FIG. 1 disposed in a mold comprising a refractory material.

Next, as illustrated in FIG. 3, the wax covered support or framework is placed into a mold containing a refractory material 16, which is subsequently solidified. Heat is then applied to melt and/or burn off the wax 12, thereby leaving a void 18 in the mold corresponding to the removed wax build up 12, as illustrated in FIG. 4.

Figure 4:
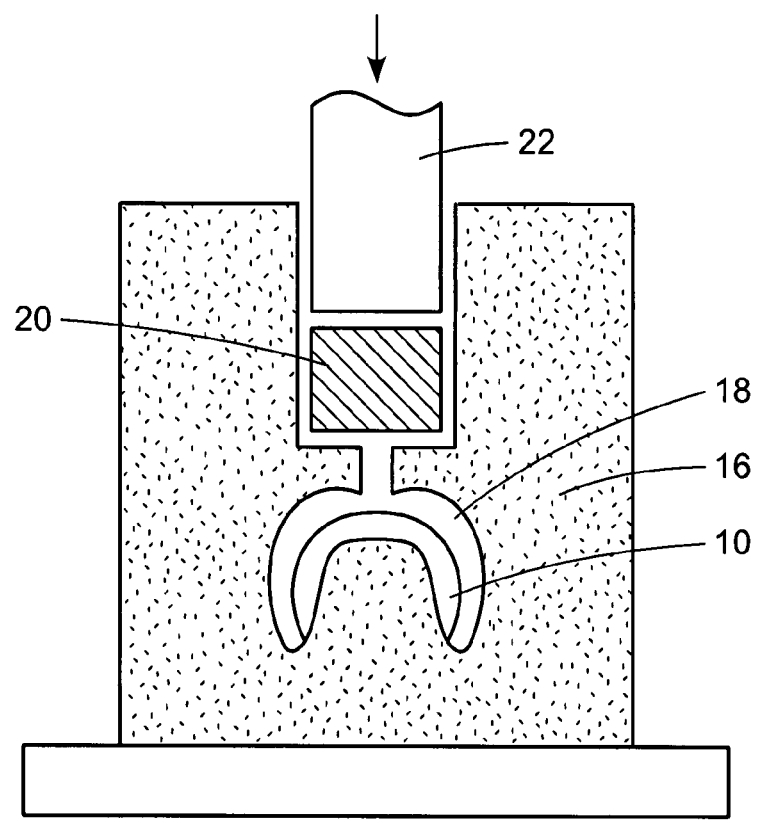
FIG. 4 is a plan view of the arrangement of FIG. 3 after the wax build-up has been removed, and with the addition of a pressable body of one embodiment of the present invention.

As further illustrated in FIG. 4, a body 20 formed from the overlay material of the present invention can be placed as illustrated. The body 20 can be formed by any suitable technique, such as described above. The body 20 can be provided with one or more of a composition, properties and/or characteristics associated with the overlay material of the present invention as described herein. The body 20 is sometimes referred to as a pellet, ingot, or the like, but can have any suitable configuration or geometry, and is not limited to the illustrated embodiment.

The body 20 is then heated to a suitable temperature in order to render it flowable upon application of a pressing force via a pressing member 22. According to one embodiment, the pressing temperature can be from about 850° C. to about 950° C. The amount of force or pressure applied by the pressing member 22 can likewise be selected to be at any suitable level. By way of non-limiting example, the pressing pressure can be less than about 1.0 MPa, or about 0.2-about 0.7 MPa, or about 0.3-about 0.6 MPa.

Figure 5:
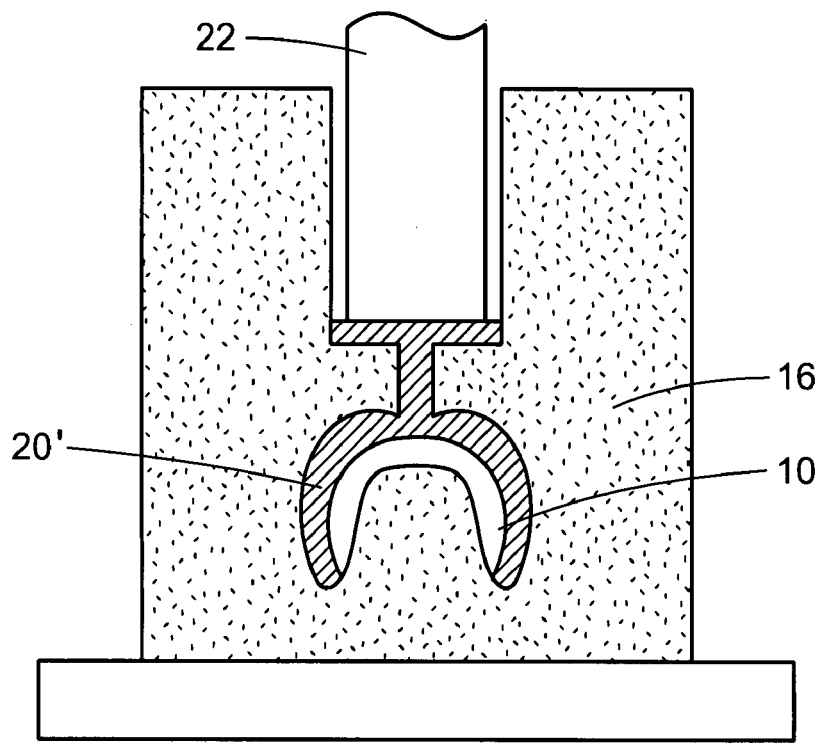
FIG. 5 is a plan view of the arrangement of FIG. 4 after the pressable body has been caused to flow into the mold.

As illustrated in FIG. 5, the above described pressing operation causes the body 20 to flow through the passage formed by the sprue 14 and into the void 18 such that it is applied to one or more surfaces of the framework 10 thereby forming an overlay 20'.

Figure 6:
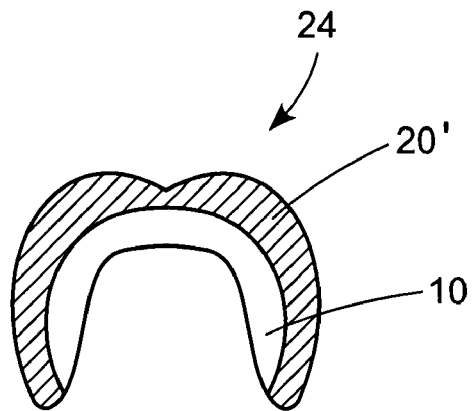
FIG. 6 is a sectional view of a dental article of the present invention.

After the overlay 20' has solidified, the covered framework or support 10 is removed from the mold, the sprue 14 removed, and any final finishing operations (e.g., glazing, etc.) are performed. The resulting dental article 24, as illustrated in FIG. 6, generally comprises a core or framework 10, and an overlay 20'. According to certain embodiments of the present invention, the overlay 20' is applied directly to the core or framework 10, and thus does not include an intervening liner. The overlay 20' is constructed of an overlay material of the type described herein.

The dental article can comprise any suitable article or configuration. A dental article of the present invention can take any suitable form. Suitable dental articles include, but are not limited to: a veneer, inlay, onlay, crown, partial crown, bridge, fixed partial denture, Maryland bridge, implant abutment or whole implant.

As mentioned above, one advantage of the present invention is that the overlay material is sufficiently strong, and bonds well to the core or framework, so that a separate layer of margin material (e.g., a margin porcelain) can be avoided.

The following examples are directed to illustrative, non-limiting optional embodiments of the present invention.

EXAMPLES 1-6

Examples 1-6 are comparative examples illustrative of the relative strength of various unreinforced aluminosilicate and alumino-borosilicate glasses, which can be used as components of pressed zirconia overlays. Compositions of Examples 1-6 were formulated to yield thermal expansion properties within the same range as commercial zirconia overlay porcelains, i.e., 8.8-10.5×10$^{-6}$/° C. at 500° C.

The various alumino-silicate glasses were melted at temperatures of 1100°-1600° C. using conventional precursors, quenched in water, dried, milled and screened to −200 mesh. Small cylinders, sometimes called pellets or ingots, of about 2 g in weight were fabricated from glass (Examples 1-6) or porcelain (Examples 7-9) powders by uniaxial dry-pressing using a channel die and sintering the resulting compacts to full density at temperatures given in Table 1 below as firing temperatures. The resulting fully-fused pellets were used to heat press ⅛" diameter short rods (20 mm in length) to measure 3-point flexure strength, and longer 2" rods to measure as-pressed thermal expansion and also to press full contour overlays onto commercially available cores or frameworks. The pressing operations were carried out at temperatures given in Table 1 below as "Pressing Temperature," using a conventional heat pressing technique, also described in U.S. Pat. Nos. 6,484,791 and 6,302,186. The cores or frameworks were waxed up to full contour and the resulting full contour pressed central crowns were mounted in a clear epoxy, sectioned, re-mounted in a clear epoxy and polished to 1 micron. Interfaces between the pressed overlay and zirconia core were qualitatively evaluated at magnifications ranging from ×50 to ×2000 and rated as very good, good, fair and poor. Compositions and properties of these glasses are given in Table 1 below. Again, compositions of Examples 1-6 were formulated to yield the thermal expansion within the same range (8.8-10.5×10$^{-6}$/° C. at 500° C.) as commercial zirconia overlay porcelains.

TABLE 1

Glass compositions (in wt. %)

| | Example No. | | | | | |
|---|---|---|---|---|---|---|
| Composition | 1<br>Glass 1 | 2<br>Glass 2 | 3<br>Glass 2Y | 4<br>Glass 3 | 5<br>Glass 4 | 6<br>Glass 2 + 1 4:1 |
| $SiO_2$ | 69.38 | 67.50 | 67.50 | 68.20 | 67.86 | 67.88 |
| $B_2O_3$ | 3.27 | 0.00 | 0.00 | 0.00 | 0.00 | 0.65 |
| $Al_2O_3$ | 4.89 | 11.27 | 11.27 | 11.20 | 13.33 | 9.99 |
| ZnO | 2.55 | 0.00 | 0.00 | 0.00 | 0.00 | 0.51 |
| CaO | 1.80 | 2.10 | 2.10 | 2.60 | 1.99 | 2.04 |
| MgO | 1.24 | 1.26 | 1.26 | 1.60 | 0.00 | 1.25 |
| BaO | 1.20 | 0.00 | 0.00 | 0.00 | 0.00 | 0.24 |
| $Li_2O$ | 0.00 | 1.02 | 1.02 | 0.00 | 0.00 | 0.82 |
| $K_2O$ | 7.49 | 6.08 | 6.08 | 7.20 | 10.15 | 6.36 |
| $Y_2O_3$ | 0.00 | 0.00 | 0.30 | 0.00 | 0.00 | 0.00 |
| $Na_2O$ | 8.18 | 10.23 | 10.23 | 9.20 | 6.17 | 9.82 |
| $TiO_2$ | 0.00 | 0.00 | 0.00 | 0.00 | 0.00 | 0.00 |
| $ZrO_2$ | 0.00 | 0.00 | 0.00 | 0.00 | 0.00 | 0.00 |
| $CeO_2$ | 0.00 | 0.55 | 0.55 | 0.00 | 0.50 | 0.44 |
| F | 0.00 | 0.00 | 0.00 | 0.00 | 0.00 | 0.00 |
| $Sb_2O_3$ | 0.00 | 0.00 | 0.00 | 0.00 | 0.00 | 0.00 |
| Firing (Pellet Sintering) Temperature, ° C. | 845 | 875 | 875 | 925 | 980 | 870 |
| Pressing Temperature, ° C. | 820 | 850 | 860 | 910 | 970 | 845 |
| CTE (r.t.-500° C.) | 8.8 | 9.7 | 9.5 | 9.0 | 8.8 | 9.4 |
| As-Pressed Flexural Strength*, MPa | 109 ± 11 | 116 ± 12 | 120 ± 13 | 119 ± 20 | 104 ± 18 | 118 ± 10 |
| Bonding to Zirconia | Good | Good | Very Good | Fair | Poor | Good |

Surprisingly it was found that glass compositions comprising MgO yielded the highest strength while glass compositions comprising $Li_2O$ in combination with MgO exhibited the best quality of the pressed interfaces with zirconia. Examples 1-6 illustrate the fairly well-known fact that unreinforced glasses are inherently brittle and weak and if used as pressing glasses will limit the resulting strength to less than 120 MPa, as taught in U.S. Patent Application Publication 2006/0099552. Therefore glasses compositions #2 and #2Y having the best combination of properties were used as glass matrix compositions to fabricate dental overlay materials and dental articles of Examples 8-14 below, which are illustrative of the present invention.

EXAMPLES 7-9

As some of the commercial overlay porcelains for zirconia contain small amounts of leucite, comparative Example 7 was to illustrate that in the amounts of less than about 10 wt % leucite is not effective as reinforcement. Examples 7-9 illustrate certain embodiments of the present invention wherein the material strength was improved by adding a reinforcement phase to the glass matrix compositions discussed above. Glass powders corresponding to glass compositions 1, 2 and 2Y in Table 1 produced as described above were mixed with various reinforcing phases to strengthen the glass matrices of the preferred compositions that have relatively high flexure strength and also bond well to zirconia and thus illustrate overlay material compositions of the invention that are both strong and bond well to zirconia, while being pressable to zirconia cores within the temperature range of 850° C.-950° C. The same type of samples were fabricated by heat pressing and the same tests were carried out as for the compositions of Examples 1-6 above. The results of all tests and observations are summarized in the Table 2 below.

porcelain composition of Example 9 comprising $Y_2O_3$ was on average 10% higher than that of $Y_2O_3$-free porcelain composition of Example 8.

EXAMPLES 11-14

Examples 11-14 illustrate the intended applications of dental overlay materials of the invention in fabrication of dental restorations with improved properties. Dental ceramic or powders produced in Examples 7-9 were not shaded and called "white porcelains," or in the industry simply called "whites." To make the finished shaded dental ceramic product, inorganic pigments were added to these white porcelain

TABLE 2

Dental ceramics for pressing onto zirconia frameworks

| | Example No. | | |
|---|---|---|---|
| | 7 | 8 | 9 |
| Matrix glass composition | Glass 1 | Glass 2 | Glass 2Y |
| Reinforcement | 10% of high expansion synthetic leucite frit (70% of leucite) with average particle size of 15 microns | 1.25 wt. % of A14* alumina with average particle size of 5 microns | 1.25 wt. % of A14* alumina with average particle size of 5 microns |
| Firing (Pellet Sintering) Temperature ° C. | 865 | 880 | 880 |
| Pressing Temperature ° C. | 860 | 870 | 870 |
| CTE (r.t. −500° C.), $10^{-6}$/° C. | 9.6 | 9.5 | 9.4 |
| As-Pressed Flexural Strength*, MPa | 97 ± 11 | 132 ± 21 | 128 ± 14 |
| Bonding to Zirconia | Good | Good | Very Good |

*From Whittaker, Clark and Daniels, NJ

The best combination of properties were attained for glass ceramics of Examples 8 and 9 based on alumino-silicate glass matrix compositions which are boron free and comprise $Li_2O$ in combination with MgO.

EXAMPLE 10

Example 10 illustrates the effect of $Y_2O_3$ on bonding to YTZP zirconia. Bonding to zirconia was quantitatively measured for dental ceramic compositions of Examples 8 and 9 by the Schwickerath crack initiation test per ISO9693 standard. First, fully-dense (25±1) mm×(3±0.1 mm×(0.5±0.05) mm strips were fabricated by sintering and sectioning Tosoh TZ-3YS-E powder compacts. Wax (a small rectangular piece of about 8×3×1 $mm^3$) was added and sprue attached to each of these strips. Following pressing and divesting the sprue was cut off, top surface of the pressed layer was polished by rubber wheel and glazed at 830° C. The final pressed, trimmed, polished and glazed ceramic thickness was within 0.86-0.99 mm. Testing was carried out and results were analyzed as described in Section 6.3.3 of ISO9693 standard incorporated by reference herein. The debonding strength of powders in the total amount from about 0.01% to about 1% by weight. The other important dimension of a final shade is opacity/translucency. In the shaded dental ceramics of this invention opacity was controlled by varying alumina content. To illustrate one of the embodiments of this invention wherein dental ceramics were shaded specifically to match the shade guide when pressed to full contour onto bare pre-shaded YTZP cores, the cores or frameworks of the most popular light shades FB1, FS2 and FS3 (Lava, 3M ESPE) were used. These cores were pressed with the overlays of the invention to produce a variety of shades matching Vita shade guide. First shaded powders and then pellets for pressing corresponding to Vita A1, A2, A3, B1, B2 and C1 shades were fabricated as described above, shades were confirmed using standard colored cores or frameworks. Pellets of the same six shades were also pressed onto other types of YTZP cores. It was surprisingly found that the FS3 shade is close enough to a base shade and A2, A3 pellets of this invention were successfully pressed to full contour onto bare shaded cores or frameworks accurately matching Vita A2 and A3 shade standards with minimal staining.

In the alternative embodiment of this invention described in Example 12 below, special core stains were developed mimicking the shades of the cores or frameworks FS1-FS7.

Application of these core stains onto white/unshaded zirconia cores/frameworks enabled use of the same pellet shades on white zirconia as on shaded zirconia resulting in the same overall shade of the finished restoration. These core stains were applied on white zirconia frameworks by hand or sprayed by air-brush forming a very thin, translucent layer of about 5-30 micron barely distinguishable as an individual layer during evaluation of the polished cross-sections under optical microscope. It was surprisingly found that spraying by air-brush resulted in coverage appearing uniform for naked eye but not microscopically continuous and rather "spotty" under microscope. This spotty wave-like interrupted layer was reminiscent of the surface texture produced by sandblasting zirconia. Such surface texture is believed to further enhance mechanical bonding of overlay to zirconia and resulted in improved aesthetics. Notwithstanding the "disappearing" thickness of these pressing stains they added enough color to the white cores to enable use of the same pellets shades.

EXAMPLE 11

A1, A2, A3, B1, B2, C1 pellets pressed to as-fired and sandblasted FS1, FS2, FS3 Lava centrals. Interfaces were qualitatively evaluated under a microscope. Shades of the dental ceramic were evaluated on finished crowns fabricated by pressing to full contour over shaded Lava (3M ESPE) copings (available from GlidewellDirect, CA). Lava substructure (core, coping) shades FS1, FS2 and FS3 were used. Table 3 below shows which shades in the Vita Shade guide were made.

TABLE 3

Coordination chart for Lava (3M ESPE) cores

| Lava core shade | Vita Shades |
| --- | --- |
| FS1 | A1, B1 |
| FS2 | B2, C1 |
| FS3 | A2, A3 |

To begin, the fit of a Lava coping was evaluated by placing it on the master die. If adjustments were made by grinding, the coping was sandblasted using 50 micron alumina at 40 psi. The coping was cleaned by steam cleaning then waxed to full contour maintaining a minimum wax thickness of 0.8 mm. Using an 8 gauge sprue, the crown was attached to the sprue base. The assembled ring former was invested using Universal™ Investment (available from Zahn Dental). Manufacturer's instructions were followed. The invested ring was placed in a burnout furnace at 1562° F. for 1 hour. After burnout, 2 pellets and a plunger were inserted into the plunger cavity of the hot ring. This assembly was transferred to the JP Auto-Press Plus furnace and pressed following the parameters in Table 4 below.

TABLE 4

Pressing Parameters

| Low Temp | 700° C. |
| --- | --- |
| Rate | 60° C. |
| Hi Temp | 860° C. |
| Hold Time | 15 min |
| Press Time | 15 min |

After pressing, the ring was cooled to room temperature then divested. Once the bulk of the investment was removed, the remaining investment was blasted off using 50 micron glass beads at 40 psi. The sprue was cut off using a diamond disc and finished with fine diamond burs.

Once all anatomy was restored, the crown was stained on the surface using artiStains™ Low Fusing Stains mixed with Universal™ Glaze Medium (both available from Zahn Dental). Various colors of stains were artistically applied in order to produce a crown whose shade matches the corresponding Vita Shade. After staining, NEW Universal™ Porcelain Glaze (available from Zahn Dental) mixed with Universal™ Glaze Medium was applied. Firing parameters for stain and glaze are in Table 5 below.

TABLE 5

Stain and Glaze Firing parameters

| Pre-Dry | 6 min |
| --- | --- |
| Low Temp | 482° C. |
| Heat Rate | 70° C./min |
| Vac | Full |
| Vac Start | 538° C. |
| Vac Stop | 774° C. |
| Hi Temp | 829° C. |
| Hold | 0 |
| Cool | 0 |

The shade of the stained and glazed full contour crown was evaluated and confirmed that it closely matched and resembled the corresponding Vita shade tab.

EXAMPLE 12

White, unshaded zirconia cores such as Cercon (Ceramco/Dentsply) and Prismatik CZ cores (both available from GlidewellDirect, CA) require special core stains to mask their white substructure. The shades of core stains were formulated to closely match Lava shaded cores as per Table 6 below.

TABLE 6

Core stains and Lava shaded cores

| Lava core | FS-1 | FS-2 | FS-3 | FS-4 | FS-5 | FS-6 | FS-7 |
| --- | --- | --- | --- | --- | --- | --- | --- |
| Core Stain # | 1 | 2 | 3 | 4 | 5 | 6 | 7 |

A special core stain shade guide visually simulating Lava discs of the same thickness was created. Each core stain was sprayed onto a fully-dense 0.5 mm disc fabricated by sintering and sectioning Tosoh TZ-3YS-E powder compacts. The CIE L*, a*, b* color coordinates of some of the stained discs were compared to Lava discs of the corresponding shade using a color spectrophotometer, Color Tec-PSM with Color Soft v.5.2.0.37D software. The CIE L*, a*, b* color readings are summarized in Table 7 below. Visually the shades of the stained disks were very similar to the corresponding Lava disks, the difference in L*a*b* readings were attributed to difference in surface texture and thickness of the corresponding disks. It should be noted that L*a*b* readings for both stained and Lava disks were within the CIE L*, a*, b* color space region associated with tooth colors. U.S. Pat. No. 6,030,209, which is incorporated herein by reference, presents the CIE L*, a*, b* color coordinates of tooth colors represented by the Vita Lumen® shade guide system manufactured by Vita Zahnfabrik (i.e., it presents the color space of tooth colors). "Tooth color" is taken to mean CIE L*, a*, b* color coordinates that fall within, or very close to, this color space.

TABLE 7

| | CIE L*, a*, b* color readings (day light D65 - 10° C.) | | | | | |
|---|---|---|---|---|---|---|
| FS#/ Core | Lava Cores (FS-1, 2, 3, 5, 7) | | | Core stains ##1, 2, 3, 5, 7 | | |
| Stain# | L | a | b | L | a | b |
| 1 | 87.00 | 0.38 | 11.62 | 86.67 | −0.90 | 15.04 |
| 2 | 85.78 | 0.54 | 15.46 | 87.23 | −0.90 | 14.26 |
| 3 | 81.18 | 2.50 | 24.85 | 82.35 | −0.11 | 25.87 |
| 5 | 79.37 | 2.86 | 26.91 | 79.62 | 0.66 | 24.92 |
| 7 | 77.27 | 1.42 | 20.10 | 78.90 | −0.13 | 23.49 |

After the white zirconia substructure was sandblasted and cleaned, these core stains were applied on white zirconia frameworks by hand or sprayed by air-brush. Comparison to a Core Stain shade guide and to a Lava substructure was done to ensure the proper application and visual appearance of the core stain shade. The stained zirconia substructure was fired according to the parameters in Table 8 below.

TABLE 8

| Core stain firing parameters | |
|---|---|
| Pre-Dry | 6 min |
| Low Temp | 500° C. |
| Heat Rate | 55° C./min |
| Vac | Full |
| Vac Start | 600° C. |
| Vac Stop | 900° C. |
| Hi Temp | 950° C. |
| Hold | 0 |
| Cool | 0 |

The same procedures from waxing to full contour to glazing the finished product were employed. The shades of the stained and glazed full contour crown were evaluated and confirmed that they closely matched and resembled the corresponding Vita shade tab.

EXAMPLE 13

The technique described above for processing single unit crowns was also used to fabricate 3-4 unit bridges and splints in the anterior region up to and including the second molar. The same procedures from cleaning the substructure to glazing the finished product were employed. The shades of the stained and glazed full contour bridges were evaluated and confirmed that they closely matched and resembled the corresponding Vita shade tab.

EXAMPLE 14

The technique described above for processing single unit crowns, bridges, and splints can also be used to fabricate restorations with substructures having various margin designs. The 360° margin was entirely or partially (i.e. on labial/buccal side) cut back up to 4 mm. These shoulder areas were waxed up and pressed producing a perfect fitting margin. An alternate margin design is wherein a 360° zirconia collar is maintained. The same procedures from waxing to full contour to glazing the finished product were employed. The shades of the stained and glazed full contour crown were evaluated and confirmed that they closely matched and resembled the corresponding Vita shade tab.

EXAMPLE 15

To illustrate the suitability of dental ceramic compositions of this invention for mass production of pellets/ingots a small pilot batch of about 500 g of the shaded dental ceramic powder (lot# J11061) corresponding to A1 shade of Example 11 above was mixed with common PVA binder in a small shear mixer and dried. The resulting agglomerated free-flowing powder was used to machine press and sinter pellets using production equipment. These pellets (lot# J28063) were used to fabricate a variety of standard dental shapes and disks to evaluate the shade fidelity and also rods and bars to determine as-pressed 3-pt bend strength and 3-pt bend strength per ISO 6872. The flexural strength per ISO 6872 of 132±16 MPa was very close to the strength of 134±11 MPa determined for as-pressed rods. For comparison the hand-pressed pellets were fabricated from the same powder (lot# J11061). Standard dental shapes heat pressed from the machine-made pellets (formed using the binderized powder) were compared in shade to the same shapes produced from hand-pressed pellets which served as control for shade assessment. The shades were found to be essentially equivalent.

For comparison the same procedures were carried out using the glass composition of Example 11 from the published U.S. Patent Application Publication No. 2004/0232576. This low-fusing glass composition containing 2.8% of $B_2O_3$ and 1.0% of $Li_2O$ with maturing temperature within the range of 760-774° C. was shaded to match A1 shade of this invention. While the hand-pressed pellets of this prior art composition closely resembled the hand-pressed and machine pressed A1 pellets of this invention, the pellets formed with the use of binder were drastically different, distinctly green-grayish resulting in unacceptable shades completely outside the dental color space.

Numbers expressing quantities of ingredients, constituents, reaction conditions, and so forth used in this specification are to be understood as being modified in all instances by the term "about". Notwithstanding that the numerical ranges and parameters setting forth, the broad scope of the subject matter presented herein are approximations, the numerical values set forth are indicated as precisely as possible. Any numerical value, however, may contain certain errors as evidenced by the standard deviation attributed to their respective measurement techniques. None of the elements recited in the appended claims should be interpreted as invoking 35 U.S.C. §112, ¶6, unless the term "means" is explicitly used.

Although the present invention has been described in connection with preferred embodiments thereof, it will be appreciated by those skilled in the art that additions, deletions, modifications, and substitutions not specifically described may be made without departing from the spirit and scope of the invention as defined in the appended claims.

We claim:

1. A pressable body comprising:
   a flexural strength of at least 125 MPa;
   is flowable at 860° C. to about 950° C.;
   at least 90 wt % of a glass matrix phase having a composition comprising $Li_2O$ and MgO and having a maturing temperature greater than 850° C.; and
   a reinforcing filler, the reinforcing filler comprising a crystalline or glass-ceramic material.

2. The body of claim 1, wherein the glass matrix composition further comprises $Y_2O_3$.

3. The body of claim 1, wherein the glass matrix composition further comprises $Al_2O_3$.

4. The body of claim 2, wherein the glass matrix composition comprises about 0.50-about 2.00 wt. % $Li_2O$, about 0.50-about 3.00 wt. % MgO, and about 0.15-about 1.00 wt. % $Y_2O_3$.

5. The body of claim 4, wherein the composition further comprises about 5-about 20 wt. % $Al_2O_3$.

6. The body of claim 1, exhibiting a coefficient of thermal expansion from about 9 to about $10 \times 10^{-6}/°$ C. from room temperature to 500° C.

7. The body of claim 1, comprising from about 1 to about 10 wt. % reinforcing filler.

8. The body of claim 7, where filler comprises at least one of: ceramic or glass-ceramic particles, whiskers and fibers.

9. The body of claim 8, wherein the filler comprises alumina.

10. The body of claim 1, wherein the body is pressable by conventional heat pressing or low pressure injection molding techniques.

11. The body of claim 1, wherein the body is pressable when placed under an applied pressure of less than about 1.0 MPa.

12. The body of claim 11, wherein the body is pressable when placed under an applied pressure of less than about 0.7 MPa.

13. The body of claim 1, wherein the body is pressable when placed under an applied pressure of about 0.2-about 0.7 MPa.

14. The body of claim 7, wherein the reinforcing filler has a coefficient of thermal expansion that differs from the coefficient of thermal expansion of the glass matrix phase by at least about $1.5 \times 10^{-6}/°$ C. from room temperature to 500° C.

15. The body of claim 7, wherein the pressable body is formed from particles thereof and sintered to near full density, and the reinforcing filler comprises a particle size, the particle size of the reinforcing filler is at least 6 times smaller than the particle size of the particles forming the body.

16. The body of claim 1, wherein the body is substantially boron-free.

17. The body of claim 1, wherein the body is substantially zinc-free.

18. The body of claim 1, further comprising one or more of: inorganic pigments, opacifying agents, fluorescent agents and opalescent agents.

19. A dental article comprising:
a first member formed from a ceramic; and
an overlay attached to the first member, the overlay formed from a material comprising:
a flexural strength of at least 125 MPa;
is flowable at 860° C. to about 950° C.; and
comprising at least a glass matrix phase having a composition comprising $Li_2O$ and MgO and having a maturing temperature greater than 850° C.

20. The dental article of claim 19, wherein the first member comprises yttria stabilized tetragonal zirconia polycrystalline material.

21. The dental article of claim 19, wherein the first member comprises a crystalline oxide ceramic.

22. The dental article of claim 19, wherein the first member comprises alumina or an alumina-zirconia composite.

23. The dental article of claim 19, wherein the overlay is directly bonded to the first member by pressing.

24. The dental article of claim 19, wherein the body is pressable when placed under an applied pressure of less than about 1.0 MPa.

25. The body of claim 24, wherein the body is pressable when placed under an applied pressure of less than about 0.7 MPa.

26. The body of claim 19, wherein the body is pressable when placed under an applied pressure of about 0.2-about 0.7 MPa.

27. The dental article of claim 19, wherein the dental article comprises a dental prosthesis comprising at least one of: a veneer, inlay, onlay, crown, partial crown, bridge, fixed partial denture, Maryland bridge, implant abutment or whole implant.

28. The dental article of claim 19, wherein the article comprises 360° or buccal/labial margins formed by the overlay.

29. The dental article of claim 28, further comprising occlusal and mesio-distal surfaces formed by the overlay.

30. The dental article of claim 19, wherein the glass matrix composition further comprises $Y_2O_3$.

31. The dental article of claim 19, wherein the glass matrix composition further comprises $Al_2O_3$.

32. The dental article of claim 30, wherein the glass matrix composition comprises about 0.5-about 2.0 wt. % $Li_2O$, about 0.5-about 3.0 wt. % MgO, and about 0.15-about 1.0 wt. % $Y_2O_3$.

33. The dental article of claim 19, wherein the overlay has a coefficient of thermal expansion of about $9\text{-}10 \times 10^{-6}/°$ C. from about room temperature to about 500° C.

34. The dental article of claim 30, wherein the overlay further comprises reinforcing filler, the reinforcing filler comprising a crystalline or glass-ceramic material.

35. The dental article of claim 34, where the filler comprises at least one of: alumina, crystalline and amorphous forms of silica, and leucite-free glass-ceramics.

36. The dental article of claim 34, comprising about 1 to about 10 wt. % of the reinforcing filler.

37. The dental article of claim 34, wherein the reinforcing filler has a coefficient of thermal expansion that differs from the coefficient of thermal expansion of the glass matrix phase by at least about $1.5 \times 10^{-6}/°$ C. from about room temperature to about 500° C.

38. The dental article of claim 34, wherein the overlay is formed by pressing particles thereof and the reinforcing filler comprises a particle size, the particle size of the reinforcing filler is at least 6 times smaller than the particle size of the particles forming the body.

39. The dental article of claim 30, wherein the overlay is substantially boron-free.

40. The dental article of claim 30, the overlay further comprising one or more of: about 0-7 wt. % $K_2O$, about 0-15 wt. % $Na_2O$, about 0-3% CaO, about 0-3% BaO, about 0-3% SrO, about 0-3% $CeO_2$, and about 0-3% $Tb_4O_7$.

41. The dental article of claim 30, wherein the pressable body further comprises about 0.01 wt. % to about 1.00 wt. % coloring agent.

* * * * *